United States Patent [19]

Grollimund et al.

[11] Patent Number: 5,432,600
[45] Date of Patent: Jul. 11, 1995

[54] SYSTEMS FOR OPTICALLY INSPECTING CYLINDRICAL SURFACES

[75] Inventors: Gary Grollimund, Chesterfield; H. Cary Longest, Jr., Midlothian; Barry S. Smith, Hopewell, all of Va.

[73] Assignee: Philip Morris Incorporated, New York, N.Y.

[21] Appl. No.: 218,041

[22] Filed: Mar. 24, 1994

Related U.S. Application Data

[63] Continuation of Ser. No. 884,746, May 15, 1992, abandoned.

[51] Int. Cl.⁶ .................................................. G01N 21/88
[52] U.S. Cl. .................................... 356/237; 356/426
[58] Field of Search .................. 356/237, 426, 73.1, 356/240; 209/535, 536; 131/208, 281, 905, 908; 359/834, 837

[56] References Cited

U.S. PATENT DOCUMENTS

| | | | |
|---|---|---|---|
| 2,446,628 | 8/1948 | Brown | 209/587 |
| 2,798,605 | 7/1957 | Richards | 356/240 |
| 2,936,886 | 5/1960 | Harmon | 209/587 |
| 3,034,645 | 5/1962 | Groppe | 209/536 |
| 3,040,179 | 6/1962 | Bolt | 250/223 |
| 3,447,679 | 6/1969 | Molins et al. | 209/535 |
| 3,527,234 | 9/1970 | Hinzmann | 131/94 |
| 3,557,374 | 1/1971 | Schmermund | 131/908 |
| 3,703,235 | 11/1972 | McEnery | 209/585 |
| 3,784,738 | 1/1974 | Natter | 178/6.5 |
| 4,011,950 | 3/1977 | McLoughlin et al. | 209/536 |
| 4,025,201 | 5/1977 | Deane | 209/939 |
| 4,208,578 | 6/1980 | McLoughlin et al. | 250/214 AG |
| 4,266,674 | 5/1981 | Bell et al. | 209/536 |
| 4,280,624 | 7/1981 | Ford | 209/585 |
| 4,377,743 | 3/1983 | Bolt et al. | 250/223 R |
| 4,398,546 | 8/1983 | Fisher et al. | 131/88 |
| 4,410,278 | 10/1983 | Makibira et al. | 356/445 |
| 4,568,970 | 2/1986 | Rockstead | 348/49 |
| 4,574,958 | 3/1986 | Manservisi | 209/535 |
| 4,579,455 | 4/1986 | Levy et al. | 356/394 |
| 4,639,592 | 1/1987 | Heitmann | 250/223 B |
| 4,645,921 | 2/1987 | Heitmann et al. | 209/536 |
| 4,652,133 | 3/1987 | Antoszewski et al. | 356/376 |
| 4,687,107 | 8/1987 | Brown et al. | 209/587 |
| 4,767,924 | 8/1988 | Giebel et al. | 250/223 R |
| 4,859,055 | 8/1989 | Gal et al. | 359/834 |
| 4,907,607 | 3/1990 | Focke et al. | 131/908 |
| 4,955,948 | 9/1990 | Focke et al. | 209/536 |
| 4,957,526 | 9/1990 | Frazee, Jr. et al. | 356/73.1 |
| 5,013,905 | 5/1991 | Neri | 209/536 |
| 5,034,822 | 7/1991 | Stevens | 359/229 |
| 5,127,737 | 7/1992 | Neri | 356/237 |
| 5,153,668 | 10/1992 | Katzir et al. | 356/237 |
| 5,175,717 | 12/1992 | Saimi et al. | 369/44.14 |
| 5,220,553 | 6/1993 | Ando et al. | 359/837 |
| 5,309,288 | 5/1994 | Kahre | 359/837 |

FOREIGN PATENT DOCUMENTS

| | | | |
|---|---|---|---|
| 472280 | 2/1929 | Germany | 209/111.5 |
| 2221029 | 1/1990 | United Kingdom | |

OTHER PUBLICATIONS

Haehner, C.B., "Inspection System for Round Objects", Western Electric Technical Digest, No. 6 (Apr. 1976), pp. 29-30.

Primary Examiner—Robert J. Warden
Assistant Examiner—Hien Tran
Attorney, Agent, or Firm—Kevin B. Osborne; James E. Schardt; Charles E. B. Glenn

[57] ABSTRACT

The entire cylindrical surface of a cylindrical object such as a cigarette is optically inspected by first inspecting at least 180° of the circumference of a first side of the surface, and then inspecting at least 180° of the circumference of the other side. Each of the inspection stations illuminates more than 180° of the circumference and images the surface from two angularly spaced directions to ensure that at least 180° of the circumference is seen at each station. Any object having a defective image is automatically rejected from the apparatus, and the images and other statistical information regarding the performance of the system are displayed by the system. The images are formed in such a way as to greatly increase the speed at which the inspection system operates so that it can keep up with the very high rates at which objects such as cigarettes are made in modern machinery (e.g., approximately 10,000 cigarettes per minute). The images are analyzed using techniques which make possible the detection of very small defects and also compensate for possible nonuniform illumination of the objects in the circumferential direction.

70 Claims, 11 Drawing Sheets

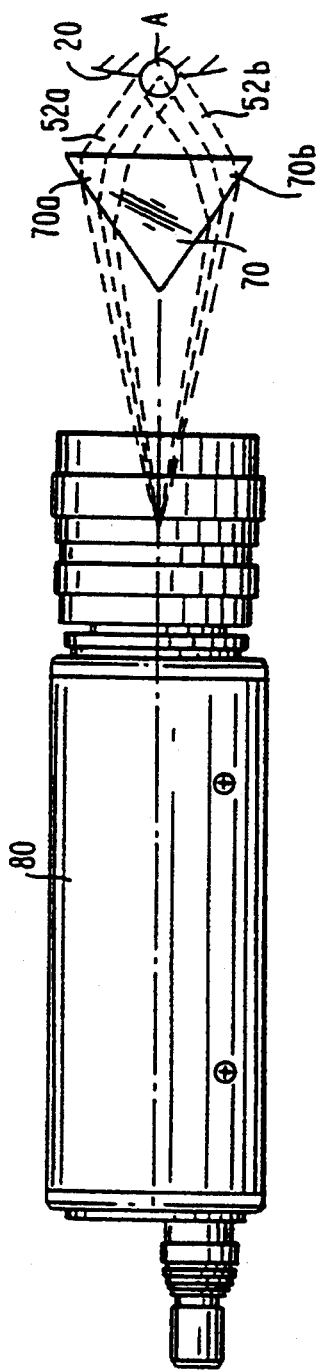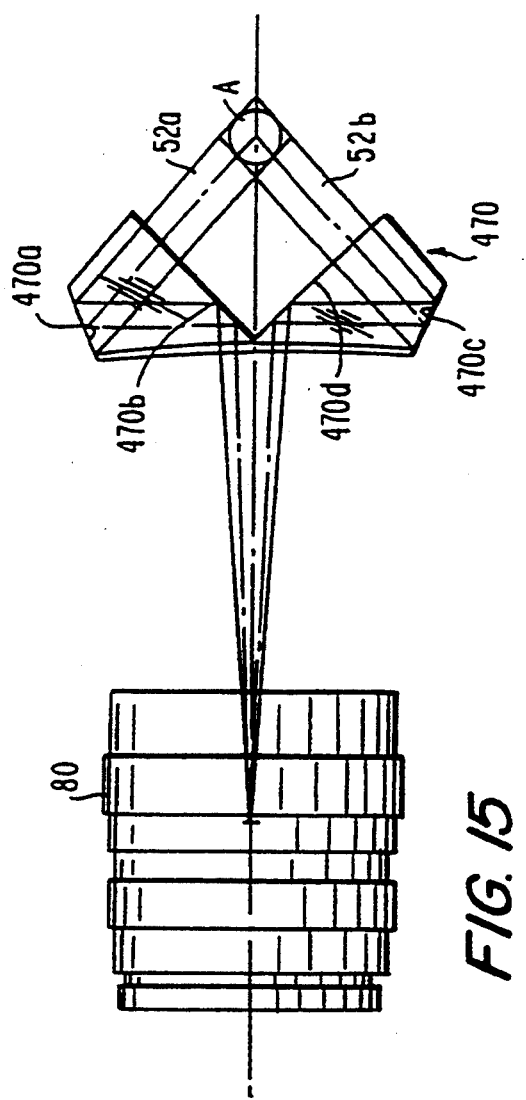
FIG. 14
FIG. 15

SYSTEMS FOR OPTICALLY INSPECTING CYLINDRICAL SURFACES

This is a continuation of application Ser. No. 07/884,746 filed on May 15, 1992, now abandoned.

BACKGROUND OF THE INVENTION

This invention relates to systems for optically inspecting cylindrical surfaces such as the cylindrical surfaces of cigarettes.

It is highly desirable to be able to inspect the entire cylindrical surface of cylindrical objects such as cigarettes. Any of a wide variety of defects may occur in such objects, and it is desirable to have automated equipment for detecting those defects so that defective objects can be rejected and/or so that any malfunctioning of the machinery producing those objects can be promptly identified and corrected. In the case of cigarettes, for example, the cylindrical surface may be defective due to a piece of tobacco stem piercing the paper, an imperfection in the way the filter has been joined to the remainder of the cigarette (including the possible complete absence of the intended filter), an imperfectly formed side seal which leaves some of the tobacco visible, a discoloration of the paper, etc.

Although inspection of this kind may take place at any stage in the production of the cigarettes, it can be advantageous to perform such inspection after processing of the individual cigarettes is complete or substantially complete. At this point in their fabrication, the individual cigarettes are most easily moved through the cigarette making machinery transverse to their length. This makes it difficult to use known cylindrical surface inspection apparatus such as that shown, for example, in Heitmann et al. U.S. Pat. No. 4,645,921, which requires the cigarettes to be passed longitudinally through the inspection apparatus.

On the other hand, with the cigarettes moving transverse to their length it is much more difficult to image the entire surface of the cigarette. For example, the cylindrical nature of the surface makes uniform illumination of the surface and elimination of shadows difficult. Thus, it may be necessary to inspect the surface piecemeal, but it is highly desirable to keep the number of inspections to a minimum in order to avoid undue proliferation of the inspection components.

It should also be noted that any successful inspection system for products such as cigarettes must be extremely fast in order to keep pace with the high speeds at which such products are typically made. For example, it is now common for a single cigarette making machine to make cigarettes at rates approaching 10,000 per minute. A successful cigarette inspection system must also be able to inspect for relatively small and/or subtle defects (e.g., a hole as small as about 0.5 millimeter in diameter or a minor discoloration of the cigarette paper).

In view of the foregoing, it is an object of this invention to improve and simplify systems for inspecting cylindrical surfaces.

It is a more particular object of this invention to provide cylindrical surface inspection systems which are capable of inspecting the entire circumference of such surfaces at very high speeds.

SUMMARY OF THE INVENTION

These and other objects of the invention are accomplished in accordance with the principles of the invention by providing cylindrical surface inspection systems in which the object having the cylindrical surface is first supported (e.g., on the surface of a first rotating drum) so that one side of the object (preferably including at least half of the circumference of the cylinder) is exposed for optical inspection along a substantial length of the object. The exposed portion of the surface is illuminated by light from two linear light sources. These two light sources are aligned with the longitudinal axis of the cylindrical surface and are spaced apart by a relatively large distance circumferentially of the cylindrical surface so that collectively they preferably illuminate at least half of the circumference of the surface. Light reflected from the surface in two radially different directions is then used to form images of the surface. The two reflected light directions are preferably intermediate the directions from which the light arrives from the two light sources. However, the two reflected light directions are preferably sufficiently widely spaced circumferentially of the cylindrical surface so that collectively they provide image information regarding at least half the circumference of the surface. Optical components are preferably provided to direct the light reflected from the above-mentioned two directions to a single camera to reduce the number of cameras required.

After passing the point at which the first side of the object is imaged as described above, the support for the object is changed to expose the other side for optical inspection. For example, the object may be transferred from the surface of the above-mentioned first rotating drum to the surface of a second rotating drum. Again, preferably at least half the circumference of the cylinder is exposed. This newly exposed portion of the surface is illuminated and imaged in the same way that the first side is illuminated and imaged. A second camera (aided by optical components similar to those mentioned above in connection with the first camera) receives the reflected light from the two directions associated with the second side of the object.

Because the images of the cylindrical surface of the object typically do not fill the entire field of view of either of the above-mentioned cameras, only the portions of the camera screens containing cylindrical surface image information are scanned. The resulting saving in scanning time greatly speeds the operation of the system.

Each partial image of the cylindrical surface is analyzed to detect any defects in appearance. Although any of a wide variety of image analysis techniques can be used, in the preferred embodiments, each image is subdivided into a plurality of regions, each of which is aligned with the longitudinal axis of the cylindrical surface, and each of which is only a relatively small fraction of the dimension of the image transverse to that longitudinal axis. The image information in each of these regions is compared to expected information for that region (e.g., on an absolute or relative basis). Aligning the regions with the longitudinal axis of the cylindrical surface and confining each region to a small fraction of the circumference of the cylinder increases the sensitivity of the system to possible variations in the illumination level of the object in the circumferential direction.

On the basis of the foregoing analysis, any object having any unacceptable image is identified and preferably rejected so that it does not continue on for the further processing to which acceptable objects are subjected.

The system also preferably includes means for displaying the images of the objects, especially the images of defective objects, so the operator of the system can observe the nature of any defects. The system may also display information regarding such statistics as the number and/or percentage of defective objects encountered.

Further features of the invention, its nature and various advantages will be more apparent from the accompanying drawings and the following detailed description of the preferred embodiments.

BRIEF DESCRIPTION OF THE DRAWINGS

FIG. 14 shows an alternative embodiment of a portion of FIG. 2 in accordance with this invention.

FIG. 15 shows another alternative embodiment of a portion of FIG. 2 in accordance with this invention.

DETAILED DESCRIPTION OF THE PREFERRED EMBODIMENTS

Although the principles of this invention are equally applicable to inspecting the cylindrical surfaces of other types of objects, the invention will be fully understood from the following explanation of its application to inspecting the cylindrical surfaces of finished or substantially finished cigarettes. Similarly, it will be understood that the particular cigarette making machine implementation described below is merely illustrative of a preferred implementation of this kind, and that the invention is equally applicable to other cigarette making machine configurations.

Figure 1:
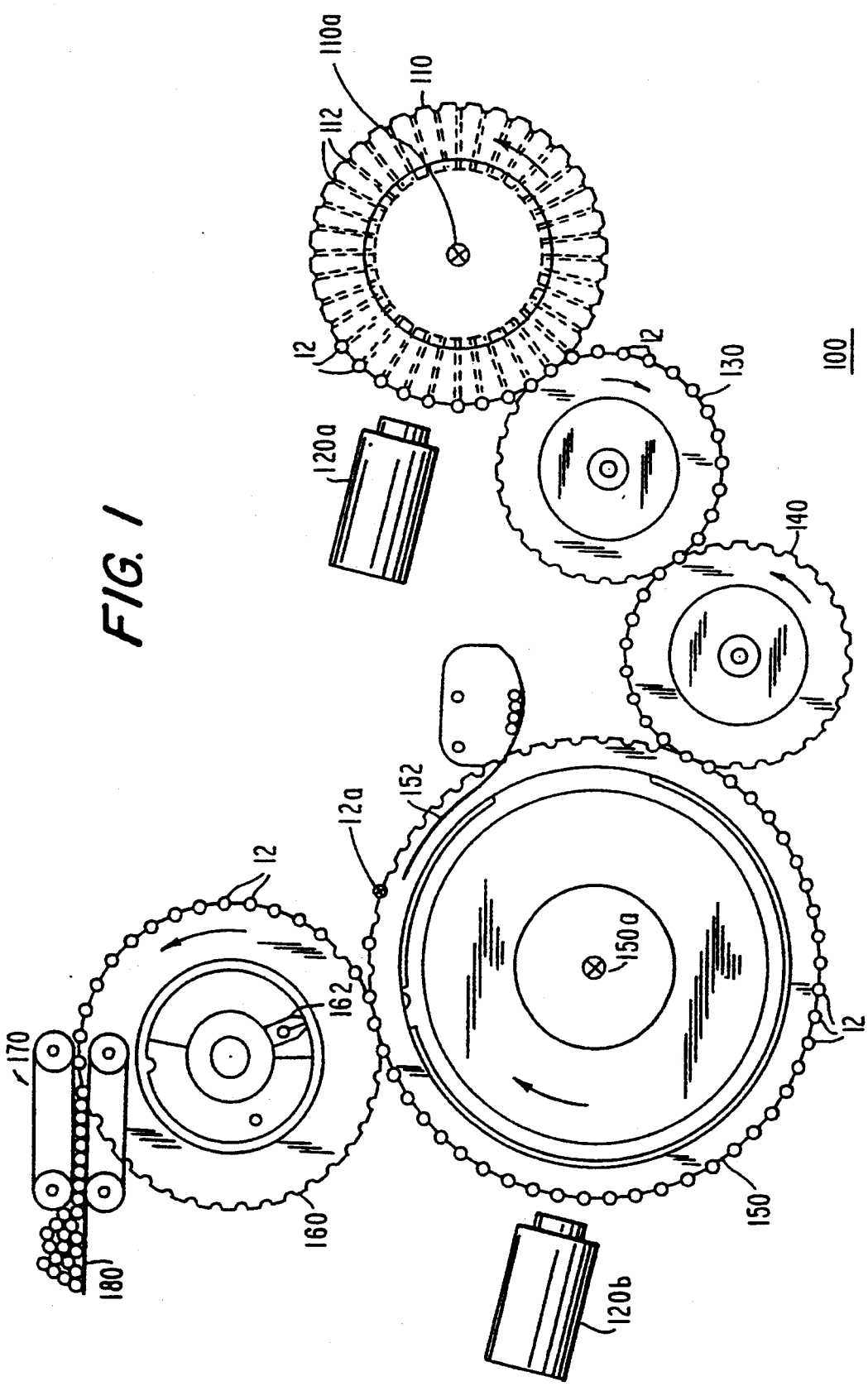
FIG. 1 is a simplified elevational view of illustrative cylindrical surface inspection apparatus constructed in accordance with this invention.

FIG. 1 shows the final portion 100 of a conventional Max S cigarette tipping machine which has been modified to include the present invention. The Max S machine is manufactured by Hauni-Werke Korber & Co. KG. of Hamburg, Germany. By the time cigarettes 12 reach the portion of the machinery shown in FIG. 1, the fabrication of the cigarettes is complete and it remains only to inspect them. Accordingly, as is conventional, the finished cigarettes are deposited one after another on conventional rotating inspection drum 110 which rotates about an axis 110A extending perpendicularly to the plane in which FIG. 1 is drawn. Inspection drum 110 has a plurality of circumferentially spaced, axially extending flutes 112 on its outer surface each flute having a longitudinal axis 12A parallel to the rotation axis of its associated drum. Each flute receives one cigarette 12, and the cigarette is held in the flute by reduced pressure ("vacuum") which is communicated to the bottom of the flute by passageways extending radially to the flute from a vacuum plenum in the interior of the drum. Such vacuum is typically applied only throughout the portion of the circumference of the drum to which the cigarettes are to be held as the drum rotates to convey the cigarettes. When a flute reaches the angular location at which the cigarette in that flute is to be transferred to another drum, the vacuum to that flute is cut off so that the next drum can pick up the cigarette with no resistance from the first drum. It will be noted that flutes 112 are shallow enough so that more than half the circumference of each cigarette is exposed.

While the cigarettes are on inspection drum 110 they are inspected in the conventional way by inspection apparatus (not shown) which is part of the Hauni machinery. For example, a typical conventional inspection test is a "dilution check" to make sure that the cigarette has the proper resistance to longitudinal air flow.

In addition, while the cigarettes are on drum 110, they also pass dual image camera box 120a which is part of the optical inspection system of this invention. As will be described in more detail below, camera box 120a illuminates more than 180° of the circumference of the cylindrical surface of each cigarette passing in front of it and forms two angularly spaced images of that surface. These two images collectively cover more than 180° of the circumference of the cylindrical surface of the cigarette. It should be noted that camera box 120a is preferably located adjacent to an upper portion of the circumference of inspection drum 110, and that it is also preferably angled down toward the cigarette which is being illuminated and imaged. This helps keep any dust and debris from accumulating on the front of box 120a (i.e., the side directed toward the cigarettes). Such dust and debris could interfere with proper illumination and imaging of the cigarettes in accordance with this invention.

After passing camera box 120a, the cigarettes are transferred from inspection drum 110 to conventional reject drum 130. Drum 130 is a rotating, fluted, vacuum drum like drum 110. Any cigarette which the conventional Hauni inspection apparatus has found to be defective on drum 110 is blown off reject drum 130 and thereby rejected in the conventional way by conventional Hauni reject apparatus (not shown). Cigarettes found to be defective by the optical inspection apparatus of this invention are rejected at a later point as is explained below.

After passing approximately half way around reject drum 130, the cigarettes are transferred to conventional transfer drum 140. Transfer drum 140 is another rotating, fluted, vacuum drum like the previously described drums. Drum 140 conveys cigarettes 12 from reject drum 130 to elevator drum 150.

Elevator drum 150 is still another substantially conventional, rotating, fluted, vacuum drum like those described above which rotates about an axis 150A extending perpendicularly to the plane in which FIG. 1 is drawn, although certain modifications of drum 150 in accordance with this invention are discussed below. Elevator drum 150 conveys cigarettes 12 from transfer drum 140 past a second dual image camera box 120b of this invention to stacker drum 160. Camera box 120b may be substantially identical to box 120a. Accordingly, box 120b illuminates more than 180° of the exposed cylindrical surface of each cigarette passing box 120b on drum 150, and also forms two angularly spaced images of that surface. Again, these two images cover more than half the circumference of the cigarette surface. It will be noted, however, that the side of each cigarette exposed on drum 150 is diametrically opposite the side which is exposed on drum 110. Accordingly, the four images formed by camera boxes 120a and 120b collectively cover the entire circumference of the cylindrical surface of each cigarette. Indeed, each of these four images preferably overlaps the two circumferentially adjacent images to some extent to ensure that no part of the circumference of any cigarette is uninspected. It will also be noted that camera box 120b is adjacent to an upper portion of drum 150, and that box 120b is angled down toward the cigarette that is being illuminated and imaged by that box. As in the case of camera box 120a, this helps keep dust and debris from accumulating on the front of box 120b and interfering with the performance of the box. Associating camera boxes 120a and 120b with two widely spaced drums 110 and 150 (i.e., drums which are spaced apart by two other drums 130 and 140) facilitates positioning both of the camera boxes so that they are adjacent to the upper portion of a drum and directed downwardly so that neither accumulates dust and debris.

By the time each cigarette is approaching the top of elevator drum 150, the optical inspection apparatus of this invention has completed its inspection and analysis of the cigarette and has made a determination as to whether or not the cigarette has an acceptable appearance. If the appearance of the cigarette is acceptable, the cigarette is transferred from elevator drum 150 to stacker drum 160. On the other hand, if the appearance of the cigarette is not acceptable, transfer of the cigarette from drum 150 to drum 160 is prevented by a brief blast of pressurized air from inhibit transfer port 162 (see commonly assigned, concurrently filed application Ser. No. 07/884,741 filed May 15, 1992). Accordingly, the defective cigarette remains on drum 150. Drum 150 is modified so that the vacuum, which is turned off adjacent to the nip between drums 150 and 160, is turned on again immediately beyond that nip. This holds any defective cigarettes which do not transfer to drum 160 to drum 150. These defective cigarettes are conveyed by drum 150 to stripper 152 which strips the defective cigarettes from the drum in order to reject them. The cigarettes extend axially beyond both end faces of drum 150 so that fingers of stripper 152 adjacent to those end faces can engage the cigarettes and strip them from the drum. The rejected cigarettes collected by stripper 152 are conveyed out of the machine (e.g., by pressurized air flowing through the stripper).

Returning to the discussion of drum 160, cigarettes which have not been rejected by either the conventional Hauni reject mechanisms associated with reject drum 130 or the above-described reject mechanism of this invention transfer to drum 160 and are conveyed by that drum to the conventional stack forming region 170 of the machine. Stack former 170 removes the cigarettes from drum 160 and forms them into a stack for conveyance by mass flow conveyor 180. Alternatively, a conventional tray filler may be used to fill trays with the cigarettes removed from drum 160.

Figure 2:
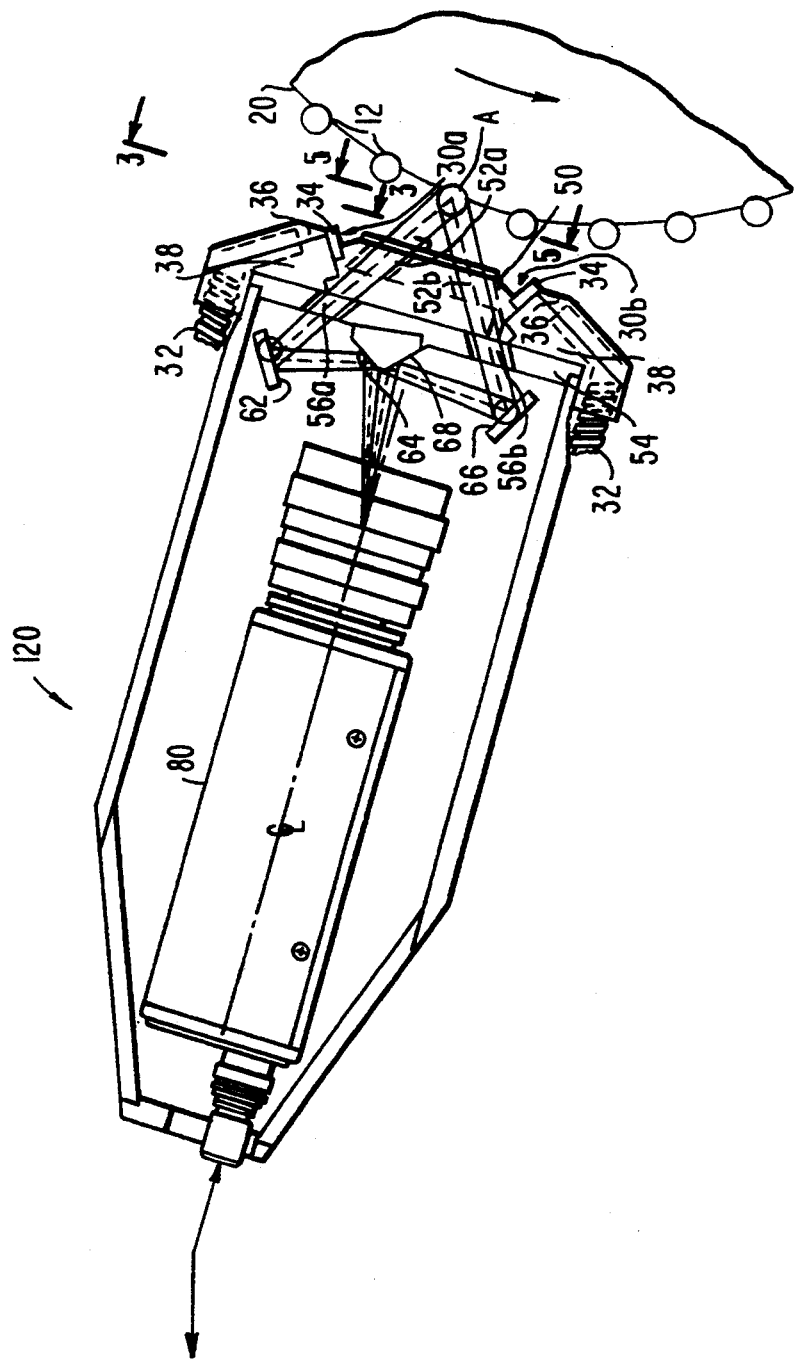
FIG. 2 is a more detailed view of a representative portion of the apparatus of FIG. 1.

Turning now to a more detailed consideration of the construction and operation of dual image camera boxes 120a and 120b, the major components of a typical one of such boxes are shown in FIG. 2. Box 120 in FIG. 2 may be either box 120a or box 120b in FIG. 1. Similarly, drum 20 in FIG. 2 may be either drum 110 or drum 150 in FIG. 1. Although shown rotating counterclockwise in FIG. 2, drum 20 may rotate in either direction in front of box 120.

As drum 20 revolves, it positions cigarettes 12 one after another midway between two linear light sources 30, respectively identified as 30a and 30b, associated with camera box 120. In FIG. 2 the cigarette identified by the letter A is thus positioned midway between the light sources. The linear axis of each of light sources 30 is substantially parallel to the longitudinal axis of cigarette A (i.e., perpendicular to the plane in which FIG. 2 is drawn). Although light sources 30 may illuminate any substantial portion of the length of cigarette A (e.g., at least a length greater than the circumference of the cigarette), in the depicted preferred embodiment light sources 30 illuminate the entire length of the cigarette. Both of light sources 30 are aimed at the cylindrical surface of cigarette A. However, light sources 30 are spaced apart quite widely in the circumferential direction around cigarette A. Accordingly, light sources 30 collectively illuminate the entire exposed surface of cigarette A. For example, in the particular embodiment shown in FIG. 2 the angle between light sources 30 is approximately 118° so that approximately 270° of the circumference of cigarette A is illuminated by the combined effect of the two light sources. The illumination of cigarette A from light sources 30 is preferably both axially and circumferentially quite uniform and free from shadows (e.g., from cigarette A itself and from other cigarettes which are circumferentially adjacent to cigarette A on drum 20).

Figure 3:
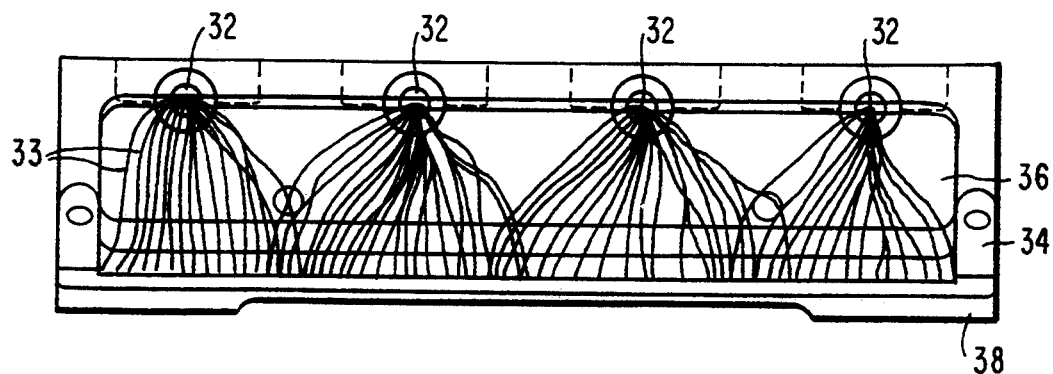
FIG. 3 is a view taken along the line 3—3 in FIG. 2.
Figure 4:
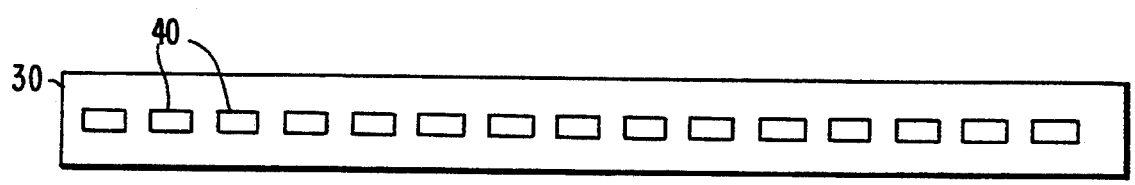
FIG. 4 is a simplified elevational view of a component which can be used in place of the component shown in FIG. 3.

Light sources 30 may be provided in any of several ways. In the embodiment shown in FIGS. 2 and 3, for example, optical fibers are used. The ends 33 of several bundles 32 of optical fibers are fanned or combed out in a linear array behind a translucent plastic (e.g., Lexan) strip 34. This array of optical fibers is stabilized and aimed at cigarette A by being clamped between members 36 and 38. Strip 34 somewhat diffuses the light from the optical fibers to help promote uniform illumination of cigarette A. As an alternative (shown in FIG. 4), each light source 30 could be formed of a line of light emitting diodes 40.

Although the illumination produced by light sources 30 is described above as axially uniform, the light produced by these light sources can be "programmed" in various ways if desired. For example, to compensate for a possible difference in the distance between light sources 30 and cigarette A, the farther light source could be illuminated more brightly. Similarly, to enhance or deemphasize certain features or regions of cigarette A, corresponding axial portions of light sources 30 could be illuminated more or less brightly than other axial portions. Not all of each light source 30 may need to be illuminated at the same time, but instead the illumination could "scan" along the length of the light source. The "color" of light sources 30 can also be selected as desired. For example, it may be desired to use infrared (IR) light sources combined with IR filtering of the light reflected from cigarette A in order to reduce or eliminate disturbances from ambient light.

Regardless of the structure of light sources 30, they are preferably strobed (i.e., briefly illuminated) each time a cigarette is properly positioned between them on drum 20. This has the effect of "freezing" the motion of the cigarette being inspected.

Figure 5:
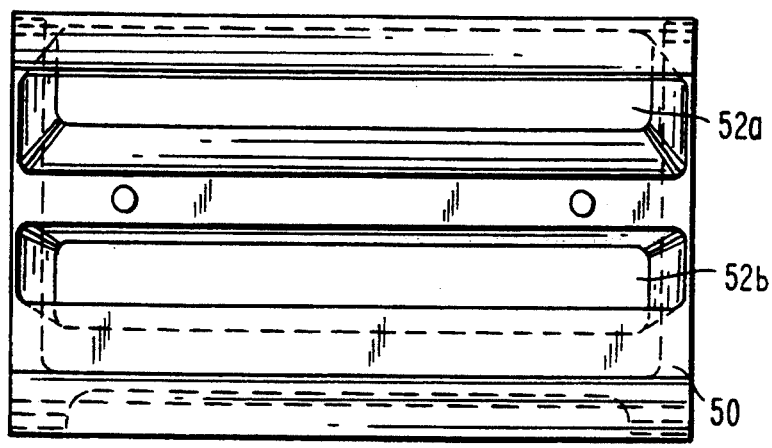
FIG. 5 is a simplified view taken generally along the line 5—5 in FIG. 2.

Light reflected from two circumferentially different (although preferably immediately adjacent or even somewhat overlapping) regions of cigarette A illuminated by light sources 30 passes through apertures 52a and 52b in aperture plate 50 which is located between light sources 30 opposite cigarette A. Like light sources 30, apertures 52 are preferably linear and parallel to the longitudinal axis of cigarette A (see also FIG. 5). Although apertures 52 could be shorter (e.g., in the event that light sources 30 illuminate only a portion of the length of cigarette A), in the depicted preferred embodiment in which light sources 30 illuminate the full length of cigarette A, apertures 52 are also long enough to pass light reflected from the entire length of the cigarette. The thickness of aperture plate 50 and the sizes and shapes of apertures 52 are preferably chosen to mask light reflected from extraneous surfaces such as the surfaces of the cigarettes adjacent to cigarette A on drum 20. In addition, the masking effect of apertures 52 is preferably enhanced by another aperture plate 54 behind plate 50 with apertures 56 that are optically aligned with apertures 52 to thereby effectively increase the thickness of plate 50. Although between light sources 30 and therefore closer together than the light sources, apertures 52 are nevertheless spaced sufficiently far apart circumferentially of cigarette A so that collectively they pass light reflected from at least half (and preferably somewhat more than half) the circumference of that cigarette. For example, in the particular embodiment shown in FIG. 2 the angle between the optical paths defined by apertures 52 is approximately 57° so that approximately 240° of the circumference of cigarette A is imaged by the combined effect of these two apertures.

The reflected light passing through aperture 52a is directed to one portion of the photosensitive image surface of conventional video camera 80 by mirrors 62 and 64. Similarly, the reflected light passing through aperture 52b is directed to another portion of the image area of camera 80 by mirrors 66 and 68. Accordingly, camera 80 receives image information for at least half (preferably more than half) the circumference of the surface of cigarette A and produces a video output signal indicative of all of that image information.

In order to ensure that both of the images received by camera 80 are focused, the length of the paths along which both images travel must be the same. Mirrors 62, 64, 66, and 68 are therefore positioned to make these two image paths the same length. In addition, for reasons that will become more apparent hereafter, it may be desirable to make the images fall on a particular portion of the camera screen (e.g., on a portion of the screen which is at or near the start of the scanning sequence). This can be accomplished by appropriate choice of such factors as the locations and angles of apertures 52 and mirrors 62, 64, 66, and 68. As shown in FIG. 2, these elements are arranged such that the reflected light is non-symmetrical, i.e., angularly displaced, relative to the optical center line $C_L$ of the camera 80.

Although various types of video cameras can be employed, in the preferred embodiments in which images must be captured at very high speeds (e.g., at the rate of approximately 10,000 per minute), camera 80 is preferably a high speed, charge coupled device ("CCD") camera.

Figure 6:
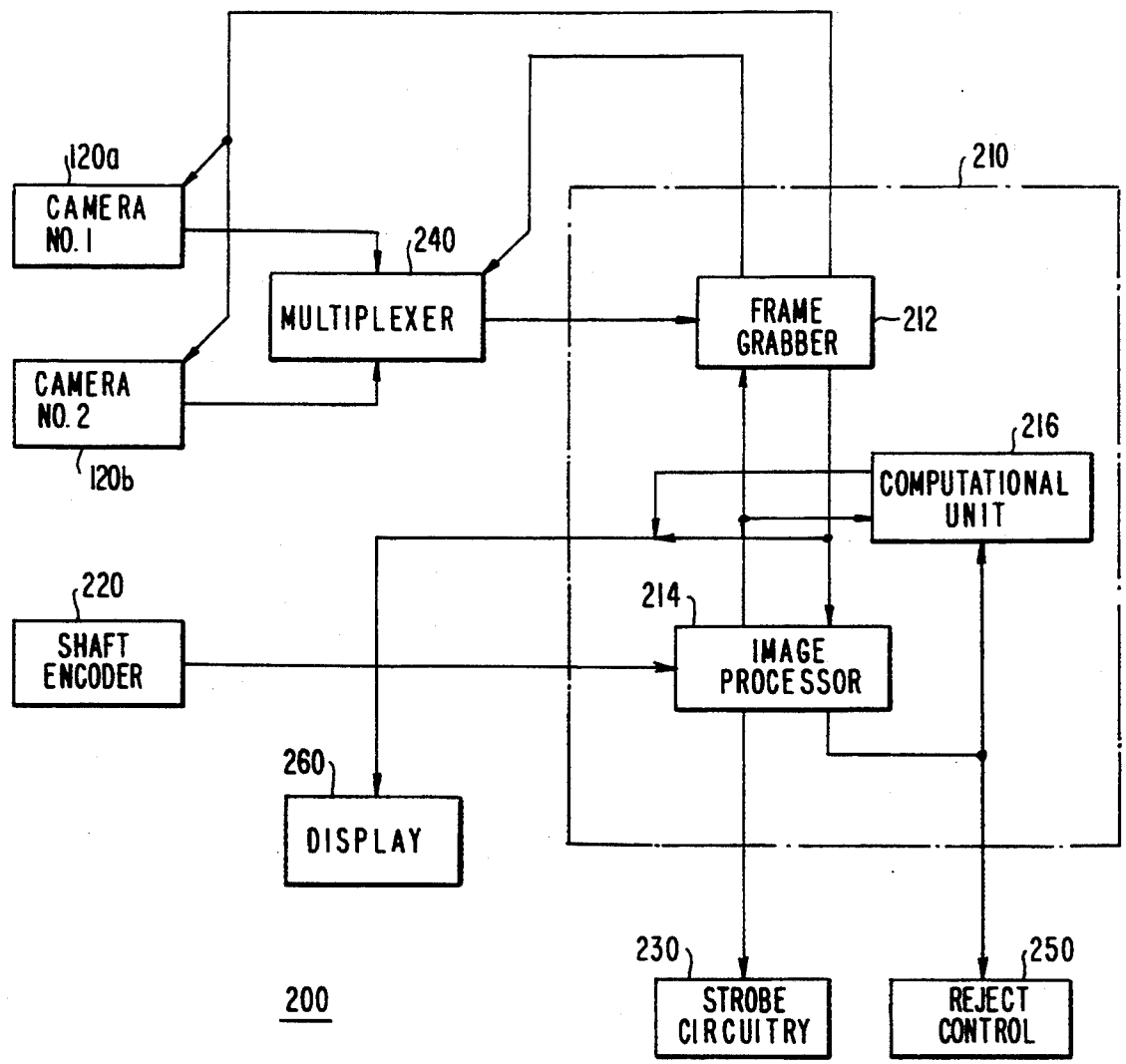
FIG. 6 is a block diagram of illustrative control and analysis apparatus constructed in accordance with the principles of this invention.

FIG. 6 shows an illustrative embodiment of control and analysis apparatus 200 for the optical inspection systems of this invention. Much of apparatus 200 is commercially available optical inspection apparatus, e.g., the 400 VPC machine vision system available from Pattern Processing Technologies, Inc. of Eden Prairie, Minn., although this apparatus has been specially adapted and programmed as discussed below in accordance with the present invention. A central component of apparatus 200 is processor 210. Processor 210 includes three major subsystems. These are frame grabber 212, image processor 214, and computational unit 216 (e.g., a conventional microprocessor).

Shaft encoder 220 is associated with the mechanical portion of the cigarette making machine (e.g., the apparatus shown in FIG. 1) and produces an output signal pulse after each predetermined increment of motion of the machinery. For example, shaft encoder 220 may be thought of as producing an output pulse each time a cigarette is positioned at location A (FIG. 2) opposite either of camera boxes 120. (Although not mentioned previously, it will be understood that camera boxes 120 are preferably positioned in FIG. 1 so that both boxes have a cigarette at the associated location A at the same time.)

Image processor 214 receives the above-mentioned shaft encoder pulses and causes the remainder of apparatus 200 to perform one complete cycle of operation in response to each pulse. In particular, in response to receipt of a shaft encoder pulse indicating that a cigarette is at position A opposite each of camera boxes 120, image processor 214 causes strobe circuitry 230 to briefly illuminate the light sources 30 of both camera boxes 120. Image processor 214 also causes frame grabber 212 to begin the scanning of the cameras 80 in both camera boxes.

As suggested above, the cigarette images captured by one of boxes 120 (e.g., box 120a) are preferably directed to the portion of the photosensitive area of the camera 80 in that box which is first to be scanned, while the cigarette images captured by the other of boxes 120 (e.g., box 120b) are preferably directed to the portion of the photosensitive area of the camera 80 in the second box which is scanned immediately after the above-mentioned portion of the first camera has been scanned. This is illustrated by FIGS. 7a and 7b, which respectively show how the cigarette images fall on the photosensitive areas of the cameras in boxes 120a and 120b in the above-described example.

Figure 7A:
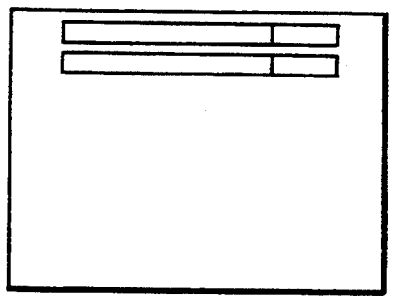
FIGS. 7a and 7b are illustrative images formed on the video cameras in the apparatus of FIG. 1 in accordance with this invention.
Figure 7B:
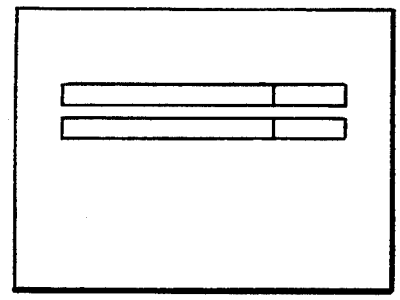
Figure 8:
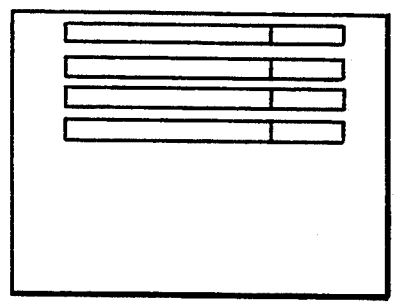
FIG. 8 shows a composite of the images of FIGS. 7a and 7b which is formed in the apparatus of FIG. 6 in accordance with this invention.

Frame grabber 212 initially controls multiplexer 240 to pass only the output signal of the camera in box 120a (assuming that the camera in that box receives the image shown in FIG. 7a). After the meaningful portion of the image captured by box 120a has been scanned, frame grabber 212 causes multiplexer 240 to switch so that it passes only the output signal of the camera in box 120b. Accordingly, the output signal of multiplexer 240 represents a composite of the FIGS. 7a and 7b images as shown in FIG. 8. Frame grabber 212 stops all scanning of the cameras in boxes 120 after all meaningful image information has been scanned. For example, in a preferred embodiment in which the photosensitive area of each camera is 640 pixels wide (parallel to the longitudinal axes of the cigarette images) by 480 pixels high, it may only be necessary to scan about 200 to 230 lines of the photosensitive areas of the cameras. The first 100 to 115 scan lines in the output signal of multiplexer 240 then come from the camera in box 120a, while the remaining 100 to 115 lines come from the camera in box 120b. The placement of the meaningful image information on the photosensitive areas of the cameras so that only portions of those areas need to be scanned, and the resulting partial scanning of the photosensitive areas, greatly increases the speed with which the system can process images.

In addition to controlling the scanning operations of the cameras in boxes 120, frame grabber 212 digitizes the analog video output signal of multiplexer 240 (e.g., by associating an appropriate one of 256 digital gray scale values with each pixel). The resulting digital image data is passed to image processor 214 for analysis to determine if the cigarette images contain any defects.

Figure 9:
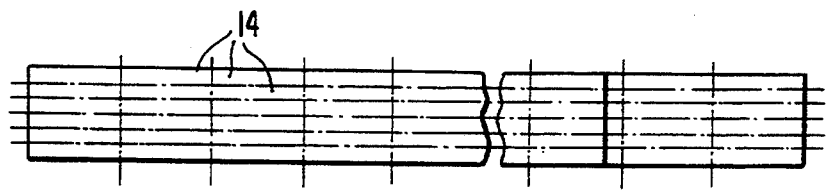
FIG. 9 is a diagram which is useful in explaining how the apparatus of FIG. 6 may analyze images in accordance with this invention.

Although image processor 214 could analyze the cigarette images in other ways, in the depicted preferred embodiment image processor 214 subdivides each cigarette image into many small regions 14 as shown, for example, in FIG. 9. Each region 14 is a rectangle having a relatively long dimension aligned with the longitudinal axis of the cigarette and a short dimension which is only a fraction of the width of the cigarette image (transverse to the longitudinal axis of cigarette). For example, each region may be 40 pixels long (parallel to the longitudinal axis of the cigarette) by two pixels wide. Use of such fairly small regions facilitates detection of relatively small image defects. Use of regions which are only a small fraction of the width of the cigarette images (perpendicular to the longitudinal axis of the cigarette) helps the system compensate or adjust for possible nonuniformity in the level of illumination of the cigarette in the circumferential direction. This latter point will become more apparent as the discussion proceeds.

Image processor 214 separately analyzes the pixel values in each of regions 14. Again, any of several techniques can be used for this analysis, but three exemplary techniques will be discussed here with reference to FIGS. 10-12. In the first technique (FIG. 10), after performing step 310 to subdivide the image into regions 14 as described above, image processor 214 compares each of the pixel values associated with a region to a predetermined threshold value associated with that region (step 320). If more than a predetermined number of pixel values are below (or alternatively above) that threshold value (steps 330 and 340), the associated image region is identified as defective (step 350). If a predetermined number of regions (e.g., one or more) are thus found to be defective (step 380), the associated cigarette is identified as defective (step 390) and is therefore rejected when it reaches the point at which it would otherwise be transferred from drum 150 to drum 160 in the apparatus of FIG. 1.

A variation of the foregoing technique (shown in FIG. 11) is for image processor 214 to compare each pixel value in each region 14 to two predetermined threshold values associated with that region (step 320'), and to count the number of pixels having values outside the range between those thresholds (step 330'). If the resulting count is more than a predetermined number (step 340), the region is identified as having a defective image (step 350).

Figure 10A:
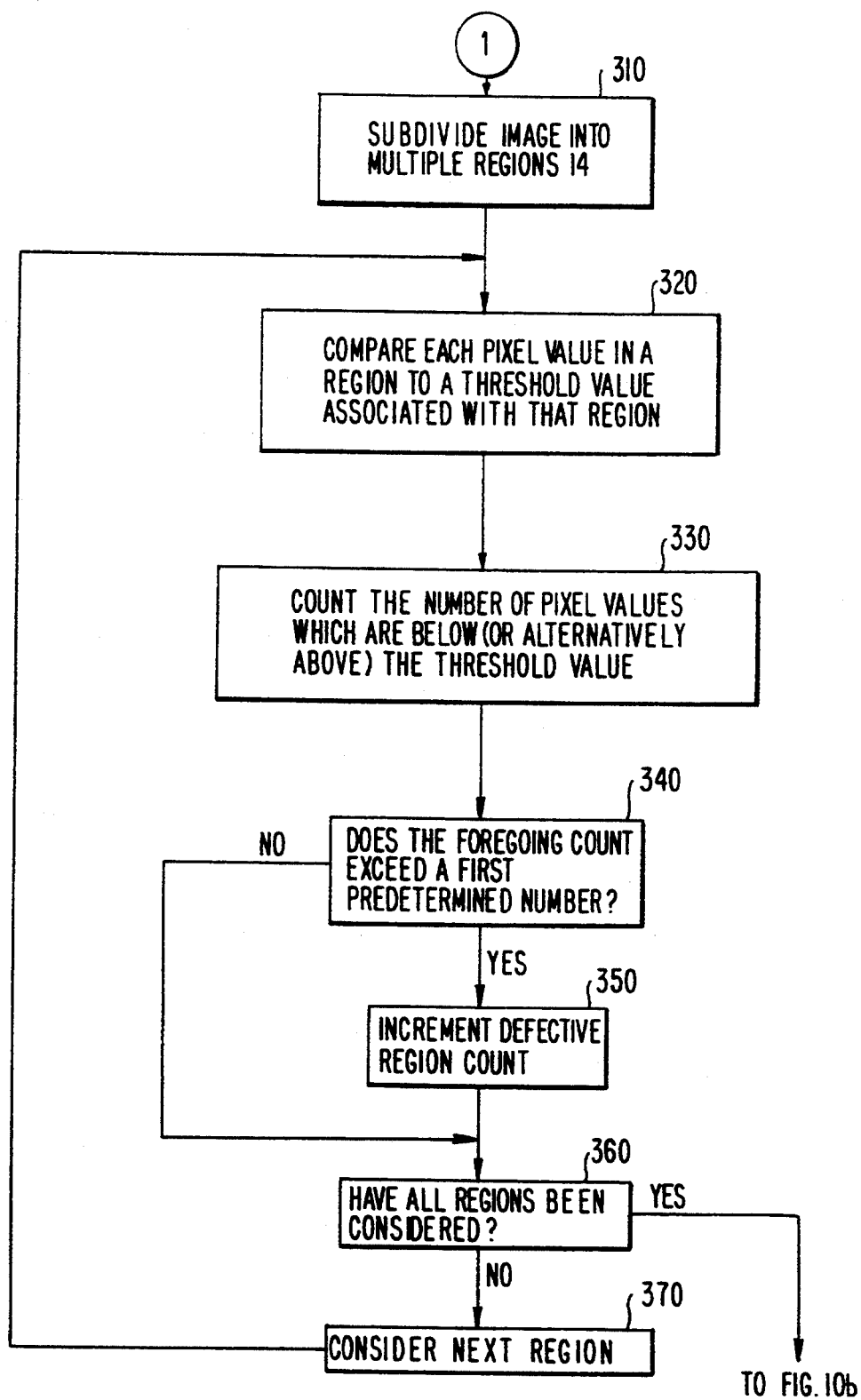
FIGS. 10a and 10b (collectively referred to as FIG. 10) are a flow chart of an illustrative image analysis process which can be carried out in the apparatus of FIG. 6 in accordance with this invention.
Figure 10B:
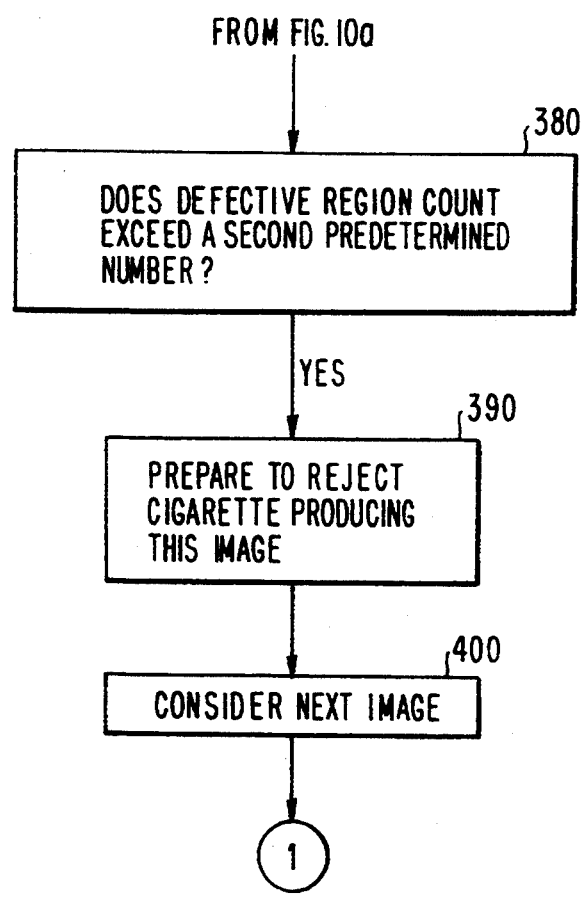
Figure 11:
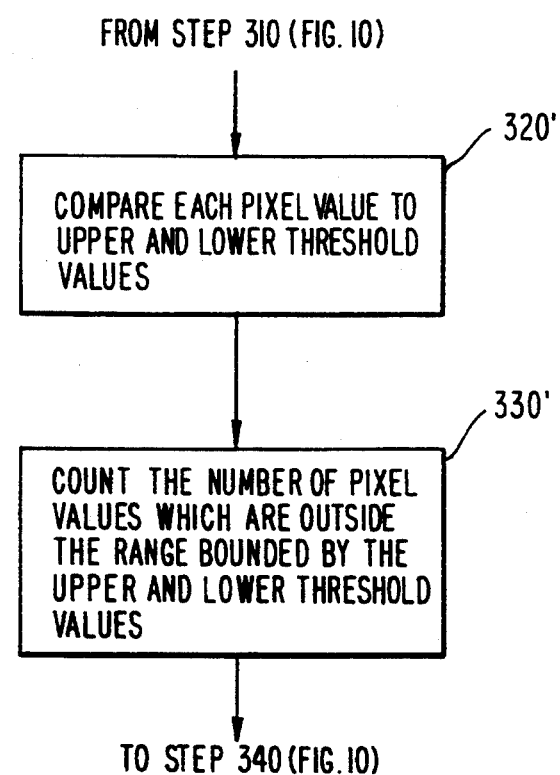
FIG. 11 is a flow chart showing how two steps in FIG. 10 can be modified to analyze images somewhat differently in accordance with the invention.
Figure 12:
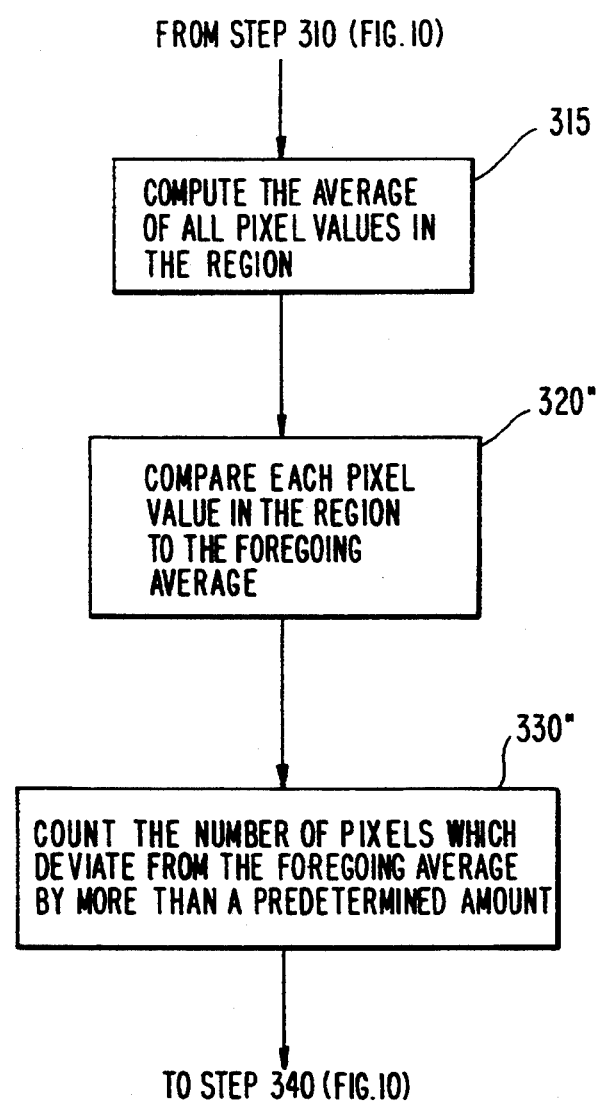
FIG. 12 is a flow chart showing another possible modification of the above-mentioned two steps in FIG. 10 in accordance with this invention.

Another technique for analyzing the pixel values in each region 14 is shown in FIG. 12. (FIG. 12 bears a similar relationship to FIG. 10 that FIG. 11 bears to FIG. 10, namely, the basic analytical process is shown in FIG. 10, but steps 320 and 330 in that FIG. are replaced by steps 320' and 330' in FIG. 11 or steps 315, 320'', and 330'' in FIG. 12.) In FIG. 12 image processor 214 computes the average of all of the pixel values in each region (step 315). Each pixel value in the region is then compared to this average (step 320''). If more than a predetermined number of pixels have values which deviate from this average by more than a predetermined amount (steps 330'' and 340), the region is identified as having a defective image (step 350). Processing then continues as described above in connection with FIG. 10. The technique of FIG. 12 helps render the apparatus insensitive to changes in illumination level from image to image.

In addition to performing overall inspection of the cigarette images for defects in appearance, the system can be used to perform other tests on the cigarette. For example, the apparatus can ensure that the length and/or diameter of the cigarette are within acceptable limits. If the cigarettes contrasts sufficiently with the supporting drum surfaces, the system can readily locate the pixel regions 14 at which the transitions between cigarette image and drum image occur. The system can then determine whether these transitions have the proper spacing side to side (cigarette diameter) or end to end (cigarette length). If not, this can form a basis for rejecting the cigarette. Other properties such as the straightness of the above-mentioned transition regions can also be tested to detect defects such as "flags" (wrapping components which are not properly or fully glued down), improperly cut ends, etc.

Whenever image processor 214 detects a defective cigarette image as described above, it records that fact (e.g., in the appropriate stage of a shift register which shifts at the same rate as the cigarettes are being imaged). Thereafter, when enough inspection cycles have elapsed for the defective cigarette to travel from the imaging location (i.e., either the location opposite camera box 120a or the location opposite camera box 120b) at which it was found to be defective to the point at which it would normally transfer from drum 150 to drum 160, image processor 214 produces a reject output signal pulse which is applied to reject control 250. Reject control 250 causes inhibit transfer port 162 (FIG. 1) to emit the above-described pressurized air pulse required to prevent the defective cigarette from transferring from drum 150 to drum 160. This causes the defective cigarette to be rejected from the machine as is explained above in connection with FIG. 1.

Figure 13:
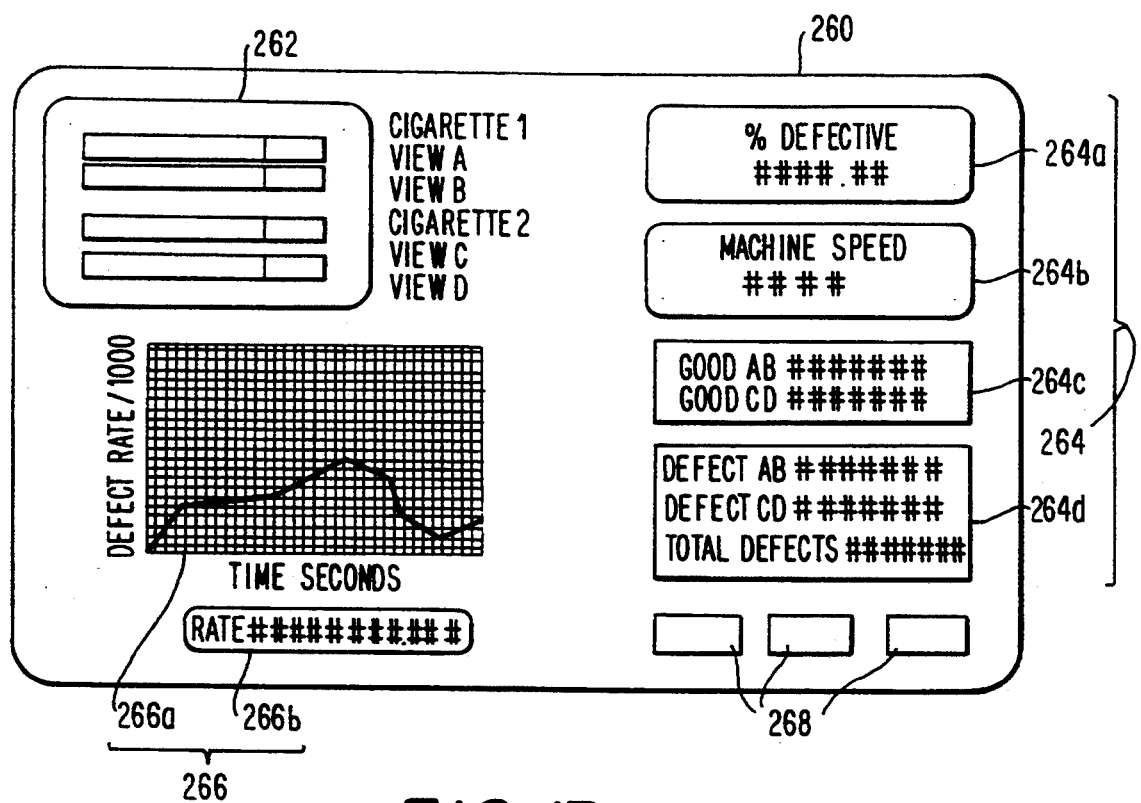
FIG. 13 is a simplified rendering of a typical display on the display component in the apparatus of FIG. 6.

In addition to inspecting and rejecting defective cigarettes, the system may also have a display 260 on which the images of the cigarettes and other data regarding the performance of the system are displayed. For example, FIG. 13 shows one possible arrangement of a video display 260. Four cigarette images are displayed in region 262. These may be the images most recently received by frame grabber 212. If desired, display 260 may hold for a few seconds any image found to be defective so that the operator of the machine can observe the defective image. Statistical information regarding the performance of the system is displayed in region 264. For example, in region 264a the percentage of defective cigarettes formed in this run may be displayed. In region 264b the current speed of the machine (e.g., in cigarettes per minute) may be displayed. In region 264c the number of good images (views A and B) received from camera box 120a and the number of good images (views C and D) received from camera box 120b in this run are displayed. In region 264d the number of defective views AB and CD, and the total number of defective views received in this run are displayed. Still other statistical information is displayed in region 266. This includes (in region 266a) a moving histogram showing the defect rate per 1000 cigarettes for the several most recent seconds of machine operation. And in region 266b a more current defect rate (e.g., the defect percentage for the most recently produced 1000 cigarettes) is displayed. Computational unit 216 (FIG. 6) may compute and provide the displayed statistical information (e.g., by counting frame initiation and reject initiation output pulses from image processor 214). Lastly, assuming that display is a so-called touch screen display, several touch screen "buttons" are displayed in region 268 for allowing the operator of the system to control certain aspects of the operation of the system (e.g., to reset the accumulation of statistical information or to modify the display in some desired way).

It will be understood that the foregoing is merely illustrative of the principles of this invention, and that various modifications can be made by those skilled in the art without departing from the scope and spirit of the invention. For example, as an alternative to the system of mirrors 62, 64, 66, and 68 shown in FIG. 2 for directing light from divergent apertures 52 to camera 80, a prism 70 may be used for this purpose as shown in FIG. 14. One operative portion 70a of prism 70 is used to redirect light (by refraction) from aperture 52a to camera 80, while another operative portion 70b of the prism is used to redirect light (by refraction) from aperture 52b to the camera. Another alternative prism embodiment 470 is shown in FIG. 15. In this alternative, light from aperture 52a enters one portion of the prism and is reflected internally off surfaces 470a and 470b in order to redirect the light toward camera 80. Light from aperture 52b enters another portion of prism 470 and is reflected internally off surfaces 470c and 470d in order to redirect the light toward camera 80.

The invention claimed is:

1. Apparatus for optically inspecting substantially an entire circumference of a reflective cylindrical surface of a cylindrical object comprising:

first object supporting means for supporting a cylindrical object so that a first side of a reflective cylindrical surface of said cylindrical object is exposed for optical inspection;

first image forming means for forming a first image of said first side, said first image including a first predetermined fraction of a circumference of said reflective cylindrical surface, said first image forming means comprising (i) first means for directing light at said first side from two directions so that light from the two directions illuminates said first side of said reflective cylindrical surface, whereby light is reflected from said first side of said reflective cylindrical surface in two directions, (ii) first means for detecting light reflected from said first side of said reflective cylindrical surface, said first light detecting means comprising a first photosensitive image area comprising more than two photosensitive sections, and (iii) first means for guiding the light reflected in one of the two directions from said first side of said reflective cylindrical surface to a first of the more than two photosensitive sections of the first photosensitive image area and for guiding the light reflected in the other of the two directions to a second of the more than two photosensitive sections of the first photosensitive image area, wherein the first image of the first predetermined fraction of the circumference of said reflective cylindrical surface is formed on the first and second photosensitive sections of the more than two photosensitive sections of first photosensitive image area;

second object supporting means for receiving said cylindrical object from said first object supporting means and for supporting said cylindrical object so that a second side of said reflective cylindrical surface is exposed for optical inspection, said second side including all portions of the circumference of said cylindrical surface which are not included in said first side; and second image forming means for forming a second image of said second side, said second image including all portions of the circumference of said reflective cylindrical surface which are not included in said first image, said second image forming means comprising (i) second means for directing light at said second side from two directions so that light from the two directions illuminates said second side of said reflective cylindrical surface, whereby light is reflected from said second side of said reflective cylindrical surface in two directions, (ii) second means for detecting light reflected from said second side of said reflective cylindrical surface, said second light detecting means comprising a second photosensitive image area comprising more than two photosensitive sections, and (iii) second means for guiding the light reflected in one of the two directions from said second side of said reflective cylindrical surface to a first of the more than two photosensitive sections of the second photosensitive image area and for guiding the light reflected in the other of the two directions to a second of the more than two photosensitive sections of the second photosensitive image area, wherein the second image of the second predetermined fraction of the circumference of said reflective cylindrical surface is formed on the first and second photosensitive sections of the more than two photosensitive sections of the second photosensitive image area.

2. The apparatus defined in claim 1 wherein said first object supporting means comprises:

a first drum having a substantially cylindrical surface which is mounted for concentric rotation about a first axis, said cylindrical surface of said first drum being radially indented by a first longitudinal flute, the longitudinal axis of said first flute being parallel to said first axis, said object being supported in said first flute so that said first side projects outward from said first flute.

3. The apparatus defined in claim 2 wherein said first axis is substantially horizontal.

4. The apparatus defined in claim 3 wherein said first image forming means is disposed relative to said first drum so that said first image forming means forms said first image while said cylindrical object is on said first drum at an upper portion of said first drum.

5. The apparatus defined in claim 4 wherein said second object supporting means comprises:

a second drum having a substantially cylindrical surface which is mounted for concentric rotation about a second axis, said cylindrical surface of said second drum being radially indented by a second longitudinal flute, the longitudinal axis of said second flute being parallel to said second axis, said object being supported in said second flute so that said second side projects outward from said second flute.

6. The apparatus defined in claim 5 wherein said second axis is substantially horizontal.

7. The apparatus defined in claim 6 wherein said second image forming means is disposed relative to said second drum so that said second image forming means forms said second image while said object is on said second drum at an upper portion of said second drum.

8. The apparatus defined in claim 7 wherein said second object supporting means further comprises:

a first rotating intermediate drum for receiving said object from said first drum after said first image forming means has formed said first image and for passing said object on toward said second drum; and at least one additional intermediate drum for receiving said object passed on from said first intermediate drum and for transferring said object to said second drum.

9. The apparatus defined in claim 1 wherein said first predetermined fraction is more than half the circumference of said reflective cylindrical surface.

10. The apparatus defined in claim 9 wherein said second image includes a second predetermined fraction of the circumference of said reflective cylindrical surface, said second fraction being more than half the circumference of said reflective cylindrical surface.

11. The apparatus defined in claim 10 wherein said first and second fractions overlap one another in two circumferentially spaced regions.

12. The apparatus defined in claim 9 wherein said first light directing means of said first image forming means comprises:

first and second illumination means for respectively illuminating said first side from said two directions which are spaced from one another circumferentially of said reflective cylindrical surface.

13. The apparatus defined in claim 12 wherein each of said first and second illumination means is a linear illumination source having a longitudinal axis substantially parallel to the longitudinal axis of said first side.

14. The apparatus defined in claim 12 wherein each of said first and second illumination means is an infrared illumination source.

15. The apparatus defined in claim 12 wherein said first light guiding means of said first image forming means comprises:

first and second reflected illumination guiding means for respectively guiding light reflected from said first side along said two directions which are spaced from one another circumferentially of said reflective cylindrical surface.

16. The apparatus defined in claim 15 wherein the two directions associated with said first and second reflected illumination guiding means are both between the two directions associated with said first and second illumination means.

17. The apparatus defined in claim 1 wherein said first light detecting means of said first image forming means comprises:

a first video camera comprising the first photosensitive image area.

18. The apparatus defined in claim 15 wherein said first means for guiding provides two optical path lengths of reflected light guided by both of said first and second reflected illumination guiding means, wherein said two optical path lengths of said first means for guiding are substantially the same between said cylindrical surface and the first photosensitive image area of said first light detecting means.

19. The apparatus defined in claim 17 wherein said first means for guiding guides the reflected light to a portion of the first photosensitive image area comprising the first and second photosensitive sections of the first photosensitive image area of said first video camera, wherein the portion is scanned to an exclusion of a remainder of the more that two photosensitive sections of said first photosensitive image area in a scanning sequence of said first video camera.

20. The apparatus defined in claim 10 wherein said second light directing means of said second image forming means comprises:

third and fourth illumination means for respectively illuminating said second side from said two directions which are spaced from one another circumferentially of said reflective cylindrical surface.

21. The apparatus defined in claim 20 wherein each of said third and fourth illumination means is a linear illumination source having a longitudinal axis substantially parallel to the longitudinal axis of said second side.

22. The apparatus defined in claim 20 wherein each of said third and fourth illumination means is an infrared illumination source.

23. The apparatus defined in claim 20 wherein said second light guiding means of said second image forming means comprises:

third and fourth reflected illumination guiding means for respectively guiding light reflected from said second side along said two directions which are spaced from one another circumferentially of said reflective cylindrical surface.

24. The apparatus defined in claim 23 wherein the two directions associated with said third and fourth reflected illumination guiding means are both between the two directions associated with said third and fourth illumination means.

25. The apparatus defined in claim 1 wherein said second light guiding means of said second image forming means comprises:

a second video camera comprising the second photosensitive image area.

26. The apparatus defined in claim 23 wherein said second means for guiding provides two optical path lengths of the reflected light guided by both of said third and fourth reflected illumination guiding means wherein said two optical path lengths of said second means for guiding are substantially the same between said surface cylindrical and the second photosensitive image area of said second light detecting means.

27. The apparatus defined in claim 25 wherein said second means for guiding guides the reflected light to a portion of the second photosensitive image area comprising the first and second photosensitive sections of the second photosensitive image area of said second video camera, wherein the portion is scanned to an exclusion of a remainder of the more than two photosensitive sections of the second photosensitive image area in a scanning sequence of said second video camera.

28. The apparatus defined in claim 1 further comprising:
   means for analyzing said first and second images in order to determine whether said cylindrical object has an acceptable appearance; and
   means for conveying said cylindrical object from said second object supporting means to different destinations depending on whether or not said means for analyzing determines that said cylindrical object has an acceptable appearance.

29. The apparatus defined in claim 28 wherein said means for analyzing comprises:
   means for subdividing each of said images into a plurality of regions, each region being only a relatively small fraction of the dimension of the associated image perpendicular to the longitudinal axis of said object; and
   means for separately processing image information in each of said regions in order to determine the acceptability of the image information in the region.

30. The apparatus defined in claim 29 wherein the image information associated with each of said regions is represented by a plurality of pixel values, and wherein said means for processing comprises:
   means for comparing each of said pixel values to a predetermined value so that said image information in that region is indicated to be unacceptable if more than a predetermined number of said pixel values have a predetermined relationship to said predetermined value.

31. The apparatus defined in claim 30 wherein said predetermined value is calculated as the average of all of the pixel values in said region.

32. The apparatus defined in claim 1 wherein said first means for guiding guides the light reflected from said first side to a portion of the first photosensitive image area which comprises the first and second photosensitive sections and which is scanned to an exclusion of additional photosensitive sections of the more than two photosensitive sections in a scanning sequence of said first light detection means in order to produce a first image output signal.

33. The apparatus defined in claim 32 wherein said second means for guiding guides the light reflected from said second side to a portion of the second photosensitive area which comprises the first and second photosensitive sections and which is scanned to an exclusion of additional photosensitive sections of the more than two photosensitive sections in a scanning sequence of said second light detection means in order to produce a second image output signal.

34. The apparatus defined in claim 33 wherein said first means for guiding guides the light of said first side to a first portion of the first photosensitive image area of said first light detecting means which is distinct from a second portion of the second photosensitive image area of said second light detecting means to which said second means for guiding guides the light of said second image.

35. The apparatus defined in claim 34 further comprising:
   means for simultaneously initiating the scanning of said first and second light detecting means; and
   means for multiplexing said first and second image output signals to produce a composite video image output signal, said composite image output signal being said first image output signal during the scanning of said first portion comprising the first and second photosensitive sections of the first photosensitive image area, and said composite video output signal being said second image output signal during the scanning of said second portion comprising the first and second photosensitive sections of the second photosensitive image area.

36. The apparatus defined in claim 1 wherein said first and second object supporting means move said cylindrical object relative to said first and second image forming means, respectively, and wherein said each of first and second light directing means of said first and second image forming means comprises:
   stroboscopic illumination means for momentarily illuminating said cylindrical object as said cylindrical object moves relative to each of said first and second image forming means in order to effectively stop the motion of said object relative to said first and second image forming means so that said first and second images of said cylindrical object are effectively still images.

37. The apparatus defined in claim 1 wherein said cylindrical object is one of a plurality of similar cylindrical objects which are handled one after another in sequence by said first and second object supporting means, and wherein said first and second image forming means are respectively disposed relative to said first and second object supporting means so that each time a first cylindrical object is positioned on said first object supporting means for formation of said first image of said first object, a second object is simultaneously positioned on said second object supporting means for formation of said second image of said second object.

38. The apparatus defined in claim 17 wherein said first means for guiding guides the reflected light to a portion of said first photosensitive image area comprising the first and second photosensitive sections of the first photosensitive image area of said first video camera, wherein the portion is relatively early in a scanning sequence of said first video camera.

39. The apparatus defined in claim 25 wherein said second means for guiding guides the reflected light to a portion of said second photosensitive image comprising the first and second photosensitive sections of the second photosensitive image area of said second video camera, wherein the portion is relatively early in the scanning sequence of said second video camera.

40. The apparatus defined in claim 1 wherein said first means for guiding guides the light reflected from said first side to a portion of the first photosensitive image area which comprises the first and second photosensitive sections and which is scanned relatively early in a scanning sequence of said first light detecting means in order to produce a first image output signal.

41. The apparatus defined in claim 40 wherein said second means for directing directs the light reflected from said second side to a portion of the second photosensitive image area which comprises the first and second photosensitive sections and which is scanned relatively early in the scanning sequence of said second light detecting means in order to produce a second image output signal.

42. The apparatus defined in claim 41 wherein said first means for guiding guides the light reflected from said first side to a first portion of the first photosensitive image area of said first light detecting means which is distinct from a second portion of the second photosensitive image area of said second light detecting means to which said second means for guiding guides the light reflected from said second side.

43. The apparatus defined in claim 42 further comprising:
    means for simultaneously initiating the scanning of said first and second light detecting means; and
    means for multiplexing said first and second image output signals to produce a composite video image output signal, said composite image output signal being said first image output signal during the scanning of said first portion comprising the first and second photosensitive sections of the first photosensitive image area, and said composite video output signal being said second image output signal during the scanning of said second portion comprising the first and second photosensitive sections of the second photosensitive image area.

44. The apparatus defined in claim 43 wherein said first portion of the first photosensitive image area of said first light detecting means is relatively earlier in the scanning sequence of said first light detecting means than the distinct second portion of the second photosensitive image area of said second light detecting means in the scanning sequence of said second light detecting means.

45. The apparatus defined in claim 1 wherein said first light guiding means comprises first means for angularly displacing the light reflected in the two directions from the first side of the cylindrical object relative to an optical center line of said first photosensitive image area of said first light detecting means.

46. The apparatus according to claim 45 wherein said second light guiding means comprises second means for angularly displacing the light reflected from the second side of the cylindrical object in the two directions relative to an optical center line of said second photosensitive image area of said second light directing means.

47. Apparatus for optically inspecting a portion of a reflective cylindrical surface of an opaque, substantially cylindrical object, said surface portion having an axial length which is substantially greater than a circumference of said cylindrical object and said reflective cylindrical surface portion extending circumferentially at least half way around said cylindrical object, all of said reflective cylindrical surface portion being inspected substantially instantaneously, said apparatus comprising:
    means for supporting a cylindrical object so that a reflective cylindrical surface portion thereof is exposed for optical inspection;
    means for directing light at said reflective cylindrical surface portion from two directions which are such that the light from said two directions collectively illuminates said reflective cylindrical surface portion, whereby light is reflected from said reflective cylindrical surface portion in two directions;
    means for detecting light reflected from said reflective cylindrical surface portion, said light detecting means comprising a photosensitive image area comprising more than two photosensitive sections; and
    means for guiding the light reflected from said reflective cylindrical surface portion in one of the two directions to a first of the more than two photosensitive sections of the photosensitive image area of said light detecting means and for directing the light reflected in the other of the two directions to a second of the more than two photosensitive sections of the photosensitive image area, the first and second photosensitive sections of the photosensitive image area defining an image portion of the photosensitive image area.

48. The apparatus defined in claim 47 wherein said means for directing light comprises first and second substantially linear light sources, each of which directs light at said reflective cylindrical surface portion from a respective one of said two directions associated with said means for directing, each of said light sources being linearly aligned with said axial length of said reflective cylindrical surface portion.

49. The apparatus defined in claim 48 wherein each of said light sources comprises:
    a plurality of optical fibers, each having an end for emitting light conducted by the associated fiber; and
    means for disposing said ends of said optical fibers in a linear array.

50. The apparatus defined in claim 48 wherein each of said light sources comprises:
    a plurality of light emitting diodes disposed in a linear array.

51. The apparatus, defined in claim 47 wherein said means for guiding the reflected light comprises first and second linear apertures, each of which passes light reflected from said cylindrical surface portion in a respective one of said two directions, each of said apertures being linearly aligned with said axial length of said surface portion.

52. The apparatus defined in claim 47 wherein said means for detecting the reflected light produces a signal indicative of said reflected light.

53. The apparatus defined in claim 52 wherein said means for detecting comprises a video camera.

54. The apparatus defined in claim 47 wherein said means for guiding reflected light comprises:
    means for defining first and second linear apertures, each of which passes light reflected from said reflective cylindrical surface portion in a respective one of said two directions associated with said means for directing, each of said apertures being linearly aligned with said axial length of said reflective cylindrical surface portion;
    wherein said means for guiding light guides light passing through each of said apertures to said light detecting means.

55. The apparatus defined in claim 54 wherein said means for guiding guides light passing through each of said apertures to the respective first and second photosensitive sections of said image portion of the photosensitive image area.

56. The apparatus defined in claim 55 wherein said linear apertures are substantially parallel to one another and laterally spaced from one another, and wherein said means for guiding comprises:

first and second mirrors for respectively reflecting light passing through said first and second apertures from different directions toward a common axis; and third and fourth mirrors on respective opposite sides of said common axis for respectively reflecting light from said first and second mirrors toward respective first and second photosensitive sections of said image portion of the photosensitive image area.

57. The apparatus defined in claim 55 wherein said means for guiding comprises at least one prism for receiving light passing through one of said apertures and redirecting that light toward said image portion of the photosensitive image area.

58. The apparatus defined in claim 57 wherein said prism has two operative portions, each of which redirects light passing through a respective one of said apertures toward said image portion of the photosensitive image area.

59. The apparatus defined in claim 58 wherein said two operative portions cause convergence of said light passing through said apertures.

60. The apparatus defined in claim 59 wherein said two operative portions cause said convergence by refraction of the light passing through said two operative portions.

61. The apparatus defined in claim 59 wherein said two operative portions cause said convergence by internal reflection of said light passing through said operative portions.

62. The apparatus defined in claim 61 wherein each of said operative portions comprises:

a first surface for internally reflecting the light from a respective one of said apertures toward the light reflected by a first surface of the other one of said operative portions; and a second surface for internally reflecting the light reflected by the first surface of said operative portion toward said image portion of the photosensitive image area.

63. The apparatus defined in claim 47 wherein said first light directing means comprises:

first and second illumination means for respectively illuminating said reflective cylindrical surface portion from two directions which are spaced from one another circumferentially of said reflective cylindrical surface.

64. The apparatus defined in claim 63 wherein said first light guiding means comprises:

first and second reflected illumination guiding means for respectively guiding illumination reflected from said reflective cylindrical surface portion along two directions which are spaced from one another circumferentially of said cylindrical surface.

65. The apparatus defined in claim 64 wherein the two directions associated with said first and second reflected illumination guiding means are both between the two directions associated with said first and second illumination means.

66. The apparatus defined in claim 53 wherein said means for guiding guides the reflected light to a portion comprising the first and second photosensitive sections of the photosensitive image area of said video camera, wherein the portion is relatively early in a scanning sequence of said video camera.

67. The apparatus defined in claim 53 wherein said means for guiding guides the reflected light to a portion comprising the first and second photosensitive sections of the photosensitive image area of said video camera, wherein the portion is scanned to an exclusion of a remainder of the more than two photosensitive sections of said photosensitive image area in a scanning sequence of said video camera.

68. The apparatus defined in claim 47 wherein said means for guiding guides the light reflected from said side to a portion of the photosensitive image area which comprises the first and second photosensitive sections and which is scanned relatively early in a scanning sequence of said light detection means in order to produce an image output signal.

69. The apparatus defined in claim 40 said means for directing directs the light reflected from said side to a portion of the photosensitive image area which comprises the first and second photosensitive sections and which is scanned to an exclusion of additional photosensitive sections of the more than two photosensitive sections in a scanning sequence of said light detection means in order to produce an image output signal.

70. The apparatus according to claim 47 wherein said light guiding means comprises means for angularly displacing light reflected from said reflective cylindrical surface portion relative to an optical center line of said photosensitive image area of said light detecting means.

* * * * *